United States Patent
Tischer et al.

(10) Patent No.: US 11,657,346 B2
(45) Date of Patent: May 23, 2023

(54) SENSOR BASED ENHANCED CUSTOMER EXPERIENCE

(71) Applicant: Ergotron, Inc., St. Paul, MN (US)

(72) Inventors: William Dale Tischer, Shoreview, MN (US); Troy Edward Townes, Minneapolis, MN (US)

(73) Assignee: Ergotron, Inc., St. Paul, MN (US)

( * ) Notice: Subject to any disclaimer, the term of this patent is extended or adjusted under 35 U.S.C. 154(b) by 77 days.

(21) Appl. No.: 16/971,622

(22) PCT Filed: Feb. 28, 2019

(86) PCT No.: PCT/US2019/020136
§ 371 (c)(1),
(2) Date: Aug. 20, 2020

(87) PCT Pub. No.: WO2019/169191
PCT Pub. Date: Sep. 6, 2019

(65) Prior Publication Data
US 2020/0387844 A1  Dec. 10, 2020

Related U.S. Application Data

(60) Provisional application No. 62/636,897, filed on Mar. 1, 2018.

(51) Int. Cl.
G06Q 10/06 (2023.01)
G16H 40/40 (2018.01)
(Continued)

(52) U.S. Cl.
CPC ....... *G06Q 10/06315* (2013.01); *G06Q 10/20* (2013.01); *G06Q 30/016* (2013.01);
(Continued)

(58) Field of Classification Search
CPC combination set(s) only.
See application file for complete search history.

(56) References Cited

U.S. PATENT DOCUMENTS 8,700,009 B2  4/2014 Quy
9,338,622 B2  5/2016 Bjontegard
(Continued)

FOREIGN PATENT DOCUMENTS

AU  2010286917 B2 * 3/2016 ........... A61B 5/0017
CN  104200418 B  3/2018
(Continued)

OTHER PUBLICATIONS

D. Kwon, M. R. Hodkiewicz, J. Fan, T. Shibutani and M. G. Pecht, "IoT-Based Prognostics and Systems Health Management for Industrial Applications," in IEEE Access, vol. 4, pp. 3659-3670, 2016, doi: 10.1109/ACCESS.2016.2587754. (Year: 2016).*
(Continued)

*Primary Examiner* — Crystol Stewart
(74) *Attorney, Agent, or Firm* — Schwegman Lundberg & Woessner, P.A.

(57) ABSTRACT

Systems and techniques for electronic telemetry-based device monitoring are described herein. A set of sensor data may be collected from a sensor array. The set of sensor data may be transmitted to a cloud service platform. A set of instructions may be received based on an evaluation of the set of sensor data. An operating parameter of the component may be adjusted using the set of instructions.

24 Claims, 5 Drawing Sheets

(51) Int. Cl.
*G06Q 10/00* (2023.01)
*G06Q 30/00* (2023.01)
*H02J 50/80* (2016.01)
*G16H 40/67* (2018.01)
*H04L 67/12* (2022.01)
*G06Q 10/0631* (2023.01)
*G06Q 10/20* (2023.01)
*G06Q 30/016* (2023.01)

(52) U.S. Cl.
CPC .............. *G16H 40/40* (2018.01); *G16H 40/67* (2018.01); *H02J 50/80* (2016.02); *H04L 67/12* (2013.01)

(56) References Cited

U.S. PATENT DOCUMENTS

| | | | |
|---|---|---|---|
| 9,741,023 | B2 | 8/2017 | Arensmeier et al. |
| 9,916,537 | B2 | 3/2018 | Ruiz et al. |
| 10,016,897 | B2 | 7/2018 | Hitchcock et al. |
| 10,110,677 | B2 | 10/2018 | Karaoguz et al. |
| 10,154,104 | B2 | 12/2018 | Woon et al. |
| 10,541,051 | B1* | 1/2020 | Farrell ................. G01R 31/396 |
| 2005/0102005 | A1* | 5/2005 | Krig .................... A61N 1/3708 607/29 |
| 2005/0278101 | A1* | 12/2005 | Lueschow ................. E02F 9/26 701/50 |
| 2006/0078859 | A1* | 4/2006 | Mullin ............... H04N 1/00042 434/219 |
| 2007/0255116 | A1 | 11/2007 | Mehta et al. |
| 2008/0200867 | A1 | 8/2008 | Bedingfield |
| 2010/0262464 | A1 | 10/2010 | Monteforte |
| 2012/0191091 | A1 | 7/2012 | Allen |
| 2014/0266713 | A1 | 9/2014 | Sehgal et al. |
| 2014/0336791 | A1 | 11/2014 | Asenjo et al. |
| 2014/0337429 | A1* | 11/2014 | Asenjo ............... G06Q 10/0637 709/204 |
| 2015/0223890 | A1* | 8/2015 | Miller .................... A61B 50/10 726/17 |
| 2017/0091634 | A1* | 3/2017 | Ritter ................. G05B 23/0262 |
| 2018/0129785 | A1* | 5/2018 | Pal ..................... A61B 5/14532 |
| 2019/0244707 | A1* | 8/2019 | Becker .................. G16H 40/67 |

FOREIGN PATENT DOCUMENTS

| | | |
|---|---|---|
| CN | 107918993 A | 4/2018 |
| CN | 111771245 | 10/2020 |
| DE | 112019001083 T5 | 2/2021 |
| FR | 3008300 B1 | 10/2018 |
| IN | 201831020949 A | 6/2018 |
| WO | WO-2019169191 A1 | 9/2019 |

OTHER PUBLICATIONS

"International Application Serial No. PCT/US2019/020136, International Search Report dated May 28, 2019", 5 pgs.

"International Application Serial No. PCT/US2019/020136, Written Opinion dated May 28, 2019", 9 pgs.

"International Application Serial No. PCT US2019 020136, International Preliminary Report on Patentability dated Sep. 10, 2020", 11 pgs.

"Canadian Application Serial No. 3,091,453, Office Action dated Oct. 14, 2021", 4 pgs.

* cited by examiner

FIG. 5

SENSOR BASED ENHANCED CUSTOMER EXPERIENCE

CLAIM OF PRIORITY

This patent application is a U.S. National Stage Application Which claims priority to PCT Application Serial Number PCT/US2019/020136, filed on Feb. 28, 2019, and published as WO 2019/169191 A1 on Sep. 6, 2019, and titled "SENSOR BASED ENHANCED CUSTOMER EXPERIENCE," which claims the benefit of priority to U.S. Provisional Patent Application Ser. No. 62/636,897, filed on Mar. 1, 2018, and titled "SENSOR BASED ENHANCED CUSTOMER EXPERIENCE," which are incorporated by reference in their entirety.

TECHNICAL FIELD

Embodiments described herein generally relate to functional monitoring of an electronic device, in some embodiments, more specifically electronic telemetry-based monitoring of an electronic device.

BACKGROUND

Electronic devices such as computer carts, electronic cabinets, electronic tables, etc. may include a variety of electronic components. The electronic components may have operational limitations that may vary based on usage of the electronic device. It may be desired to monitor the operational state and usage of the electronic device to determine when service may be necessary for an electronic component.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Data collected from sensors located on machines may be used to make decisions about a function of a machine in a factory setting to improve yield, decide when to replace a part due to a predicted malfunction, etc. With the revolution of IoT (Internet of Things), there is an even larger push of automation improvement using remote connection to sensors over the Internet. However, limiting this technology to machine-to-machine or machine-to-technician communication is missing the potential for the Internet of Things. Using the machine data to support future sales, enhance relationships with customers, improve products, as well as improve the customer's experience with manufacturers and products by predictive maintenance based on actual number of cycles or time until a component will fail may greatly reduce the customer's downtime because the maintenance may be performed proactively on a customer's schedule rather than after the component has failed and the product is no longer functional.

Along with these predictive metrics comes the benefit of using sensor data to determine if a component is over or under-engineered based on real-world usage of the product by the customer. Costs may potentially be reduced if a component is too robust—and conversely cost may be needed to increase to improve a component that fails prematurely which will ultimately be less expensive than replacing poorly designed parts or customer field returns. However, without knowing the actual uses and environments that the product may be subjected to, everything engineers develop would be a guess. With sensor data and data analysis, patterns of usage and other analytics may be used to improve products, reduce cost, increase sales, and improve the customer's experience with a no-touch required viewpoint. The customer does not have to do anything to provide the data designers need—it may all be handled automatically. And, with the improvements made in engineering, sales, and customer experience, the value of the product now has many more times the gains with data than just the product itself. This disclosure describes techniques to implement a sensor-based customer-enhancing experience.

In accordance with various techniques of this disclosure, one or more sensors may be placed in and around the product. By way of a specific non-limiting example, the product may be a medical cart used for Electronic Medical Records (EMR) data entry or medication delivery, such as aspirin or other non-narcotic medications. The sensors may be used to monitor the temperature of the room, the barometric pressure of the room, the voltage of the cart's on-board batteries, the current providing power to the on-board inverter that provides 50 or 60-Hz 120 or 230-VAC to the user's computer and monitor attached to the cart.

In some example implementations, charge and discharge cycles of the battery may be counted so that a State of Health (SOH) of the battery may be determined. For example, a typical lithium iron phosphate (LIFE) battery chemistry may have approximately 1800 charge/discharge cycles available before the battery may need to be replaced. As another example, it may be undesirable for a bright light on the cart's display or floor to disturb a sleeping patient if the room is dark. In accordance with this disclosure, sensors that interact with the room, e.g., light sensors, may control the lighting on the cart's display or external cart floor lighting based on the room's ambient lighting. Similarly, the floor lighting may be dimmed appropriately. These are just a few examples of the number and types of sensors that may be used to provide what may be valuable customer insights into the use of the product and other benefits not directly related to the basic use of the product, e.g., a medical records/medication delivery cart.

Next, the data may be transmitted from the sensors to a database for collection. In some example implementations, Wi-Fi may be a suitable transport method for hospitals, businesses and homes. Message Queuing Telemetry Transport (MQTT) is a method of organizing the data into small packets for transmission over low-power devices that rely on battery power and is ideally suited for machine-to-machine exchange of information. Using MQTT and a publish-subscribe mo may keep the overhead for network and power at a minimum.

For example, only devices needing to hear what is going on will get the message and devices will only send their information when they need to. For example, the Wi-Fi transmitter in the cart may only energize and send information when something changes (voltage, current, battery cycle, etc.) thus eliminating the old method of polling the device for information. Meaning the device (in this case a cart) was always listening for a request to send information to a server. In the publish-subscribe model the cart may wake up its Wi-Fi transmitter when it needs to say something and then go back to sleep. Those things that need to hear what is going on are always listening and not power or bandwidth constrained and may then act accordingly upon receiving the information.

Once the information is received, the data may be stored, acted upon, discarded, or whatever the need is for the given sensor information. For example, in one implementation the battery charge/discharge cycle count may be coming close to the maximum number of charge and discharge cycles on a battery chemistry before the battery will need replacing. The sensor count information may be published, the data then may be saved to a database in the "cloud" such as Amazon Web Services (AWS). Microsoft Azure, etc. where an application connected to the company's Customer Relationship Manager (CRM) software (such as Salesforce) makes decisions about what should happen based on the data.

For example, in the case of the battery charge/discharge cycle count coming close to its limit of 1800 cycles, the cycle count sensor information may be sent to the Cloud system and then to the CRM system. The CRM system may be triggered to automatically send a message to the hospital customer saying that the batter on cart number A123456 is going to need replacement in the next 7-days and that a battery has been ordered to be installed on Thursday at 2:00 pm. If that rime is not convenient, please respond with an alternate date and time. At the same time, the service provider may be notified by the CRM system what work needs to be performed, a map to the hospital, location of the cart, and tracking number of the battery that was ordered automatically by the CRM system talking to the Enterprise Resource Planning (ERP) system and parts are on its way.

After battery replacement, the sensors on the cart may let the CRM system know all is well. Invoicing or warranty paperwork may be generated as well as a thank-you note to the customer letting them know all is well. All of this occurred with predicative down-time to the customer and without the potentially-upset customer calling to say their cart is broken followed by guesses by Customer Service about what may wrong with the cart followed by conversations with the customer and the Technical Support people or even Engineering about what is going on to help solve the problem. By adding a sensor, a database, connecting the database to a CRM and ERP system, and through the Internet, a powerful customer experience is created.

Ultimately the benefit of this customer no-touch experience is a great customer experience, improvement of the technical capabilities with respect to product improvements based on real-world data, and ultimately reduction in costs to a design and manufacturing organization throughout the entire product life-cycle. Other benefits not directly related to the product but certainly may be realized are the use of the sensor data for non-cart information decisions. For example, nurse workflow improvement studies by hospital administrators based on sensors on the cart may be realized. Sensors that indicate motion and non-motion, worksurface position, room lighting, and others may be used to indicate working habits of nurses on an aggregate scale across the organization or down to individuals. These are just two simple examples of what may be done with the sensor data to bring expanded usefulness and customer satisfaction.

Figure 1:
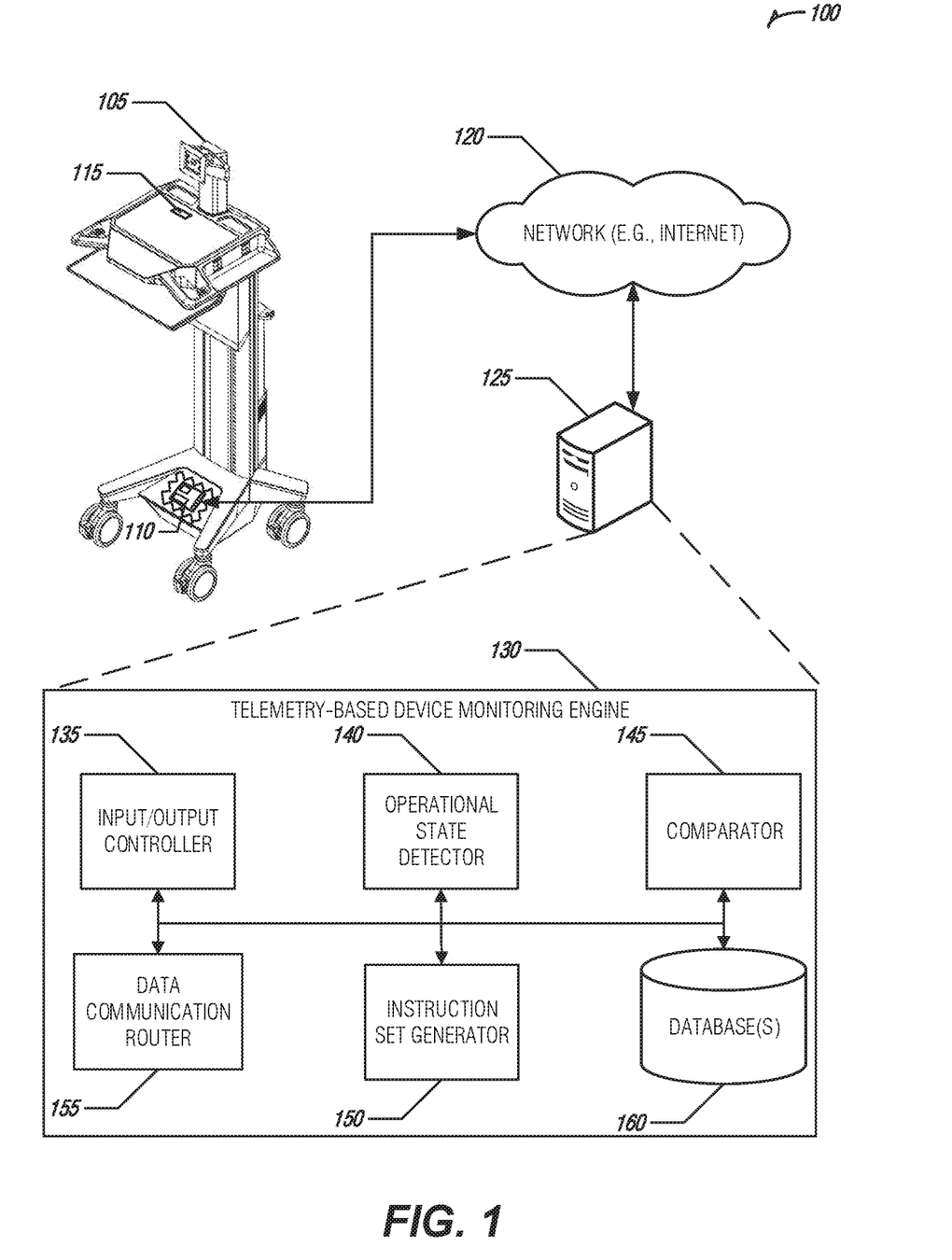
FIG. 1 is a block diagram of an example of an environment and a system for electronic telemetry-based device monitoring, according to an embodiment.
Figure 3:
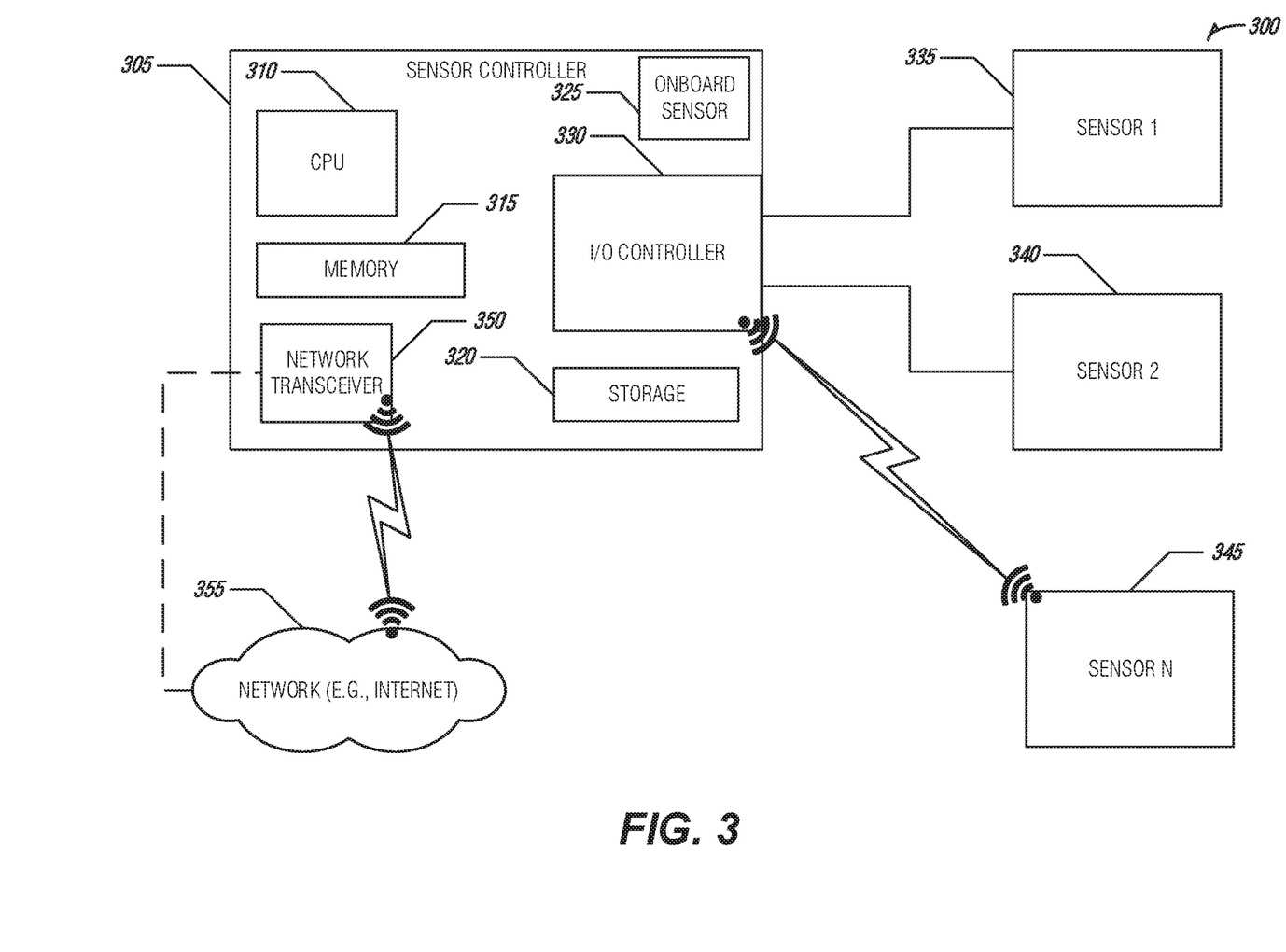
FIG. 3 is a block diagram of an example of a sensor network for electronic telemetry-based device monitoring, according to an embodiment.

FIG. 1 is a block diagram of an example of an environment 100 and a system 130 for electronic telemetry-based device monitoring, according to an embodiment. The environment 100 may include an electronic device 105 (e.g., an electronic computer cart, electronic storage cabinet, and electronic table, etc.) that includes a variety of sensors 115 (e.g., ambient light sensor, air quality sensor, a radioactivity sensor, a radiation sensor, a lighting sensor, a magnetic field sensor, a sit-stand worksurface height sensor, a height adjustment cycle sensor, a vibration sensor, an inertia, a power on/off state sensor, a voltage sensor, a temperature sensor, a current sensor, a battery cycle sensor, a drawer state sensor, a contact sensor, a barometric pressure sensor, a fault status sensor, a wireless networking operational sensor, odometer, decibel meter, oxygen sensor, motion sensor, pressure sensor, ultrasonic sensor, etc.) configured in a sensor array communicatively coupled (e.g., via a sensor network, wired connection, wired network, wireless network, short-wave radio, nearfield communication, etc.) to a sensor controller 110. A more detailed example of a sensor controller is shown in FIG. 3. The electronic device may operate in a variety of locations such as, for example, a medical treatment facility.

The sensor controller 110 may collect sensor data from the sensors and may transmit the sensor data to a cloud computing platform via the network 120 (e.g., the internet, cellular network, wired network, wireless network, etc.). The sensor data may be received by a network management server 125 (e.g., a single server, a server cluster, a system on a chip (SoC), a field-programmable gate array (FPGA), an application-specific integrated circuit (ASIC), a cloud computing platform service, etc.) via the network 120. In an example, the network management server 120 may be operating within the cloud computing platform and the cloud computing platform may facilitate transmission of the sensor data directly to the network management server 125 via the network 120.

The network management server 125 may be communicatively coupled (e.g., via wired network, wireless network, shared bus, etc.) to the system 130. In an example, the system 130 may be a telemetry-based device monitoring engine. The system 130 may include a variety of components such as an input/output controller 135, an operational state detector 140, a comparator 145, an instruction set generator 145, a data communication router 155, and database(s) 160. The components of the system 130 may be implemented in a single computing device (e.g., a server, FPGA, ASIC, SOC, a virtual server, etc.) or may be distributed across multiple computing devices (e.g., a server cluster, a cloud computing platform, a virtual server cluster, etc.).

The input/output controller 135 may obtain a set of sensor data from the sensor array included in the electronic device 105. In an example, the set of sensor data may be collected from the sensor array by the sensor controller 110 of the electronic device 105. The electronic device 105 may then transmit the set of sensor data to the cloud service platform of a cloud computing platform. The input/output controller 135 may obtain the set of sensor data from the cloud service platform. The input/output controller 135 may process e.g., format, normalize, translate, etc.) the sensor data for use as input by other components in the system 130.

By way of example, and not limitation, the set of sensor data may include sensor readings from an ambient light sensor, air quality sensor, a radioactivity sensor, a radiation sensor, a lighting sensor, a magnetic field sensor, a sit-stand worksurface height sensor, a height adjustment cycle sensor, a vibration sensor, an inertia, a power on/off state sensor, a voltage sensor, a temperature sensor, a current sensor, a battery cycle sensor, a drawer state sensor, a contact sensor, a barometric pressure sensor, a fault status sensor, a wireless networking operational sensor, odometer, decibel meter, oxygen sensor, motion sensor, pressure sensor, ultrasonic sensor, etc. In an example, the battery cycle sensor may observe a number of charging cycles that a battery in the electronic device 105 has been completed. In another example, the voltage sensor may observe the voltage level of the input power and the internal power of the electronic device 105. In another example, the ambient light sensor may observe the ambient light of an environment where the electronic device 105 is operation. In another example, the height adjustment cycle sensor may observe a number of times a lift mechanism or corresponding motor have been activated. The foregoing examples represent nonlimiting examples of sensor data that may be included in the set of sensor data. It will be readily understood that the set of sensor data may include a variety of sensor data in varying combinations. The set of sensor data may be stored in the database(s) 160.

The operational state detector 140 may work in conjunction with the comparator 145 to determine an operational state of a component (e.g., battery, motor, controller, mechanism, electronic part, etc.) of the electronic device 105 based on an evaluation of the set of sensor data. In an example, the sensor array may include a cycle sensor (e.g., battery charge cycle sensor, lift mechanism cycle sensor, etc.) for the component. The evaluation of the set of sensor data may include a comparison of a number of cycles of the component observed by the cycle sensor to a cycle threshold for the component. Upon a determination that the number of cycles is at least equal to the cycle threshold, the operational state of the component may be determined to be end-of-life (e.g., should be replaced, etc.). For example, a battery included with the electronic device 105 may have a rated duty cycle of 1800 charging cycles and an observation from a battery cycle sensor in the electronic device 105 that indicates the battery has completed 1850 charging cycles may be compared to the rated duty cycle of 1800 cycles to determine that the battery is at or near end-of life.

In an example, the operational state detector 140 may work in conjunction with the comparator 145 to predict a future failure of the component based on the evaluation of the set of sensor data. In an example, the evaluation may include a comparison of the set of sensor data to a predictive failure model for the component. For example, a machine learning model or other predictive model may be generated (e.g., trained, etc.) using training data to determine sets of sensor data that may indicate the future failure of the component. The set of sensor data may be provided as inputs to the predictive model which may then generate inputs including a likelihood of failure of the component and a predicted time before such failure is likely to occur. The predictive models may be stored in the database(s) 160.

The instruction set generator 150 may generate a set of instructions based on the operational state of the component.

The data communication router 155 may determine a recipient computing device to receive the set of instructions based on a device identifier of the electronic device 105 and a task associated with set of instructions. The input/output controller 135 may transmit the set of instructions to the recipient computing device. In an example, the input/output controller 135 may format or otherwise modify the outputs for delivery to a particular recipient computing device. For example, the set of instructions may be translated into a script file, executable file, etc based on the input requirements of the recipient computing device.

In an example, the task may be component fulfillment and the set of instructions may include instructions to transmit an electronic order for a replacement component to a supplier of the component and the recipient computing device may be an order processing computing system of the supplier. In another example, the task may be component replacement set of instructions may include instructions to transmit an electronic service workorder to a service provider of the electronic device 105 based on the device identifier of the electronic device 105 and the recipient computing device may be a workorder processing system of the service provider.

In another example, the recipient device may be a portable device associated with the device identifier and the set of instructions may include instructions that cause the portable device to display operational data for the electronic device 105 including the operational state of the component. In another example, the recipient device may be a computing device associated with an owner of the electronic device 105 based on the device identifier and the set of instructions may include instructions that cause the computing device associated with the owner to store operational data for the electronic device 105 including the operational state of the component. In yet another example, the recipient device may be a customer relationship management computing device and the set of instructions may include instructions that cause the customer relationship management computing device to store operational data for the electronic device 105 including the operational state of the component in a record associated with an owner of the electronic device 105 based on the device identifier.

Automated remote detection of the operational status of the electronic device 105 and the instruction delivery may reduce downtime of the electronic device 105 by dispatching replacement components, service, and parameter changes before an actual component failure. This may be critical in a healthcare environment as equipment downtime may compromise patient health and safety as well as the health and safety of medical professionals.

Figure 2:
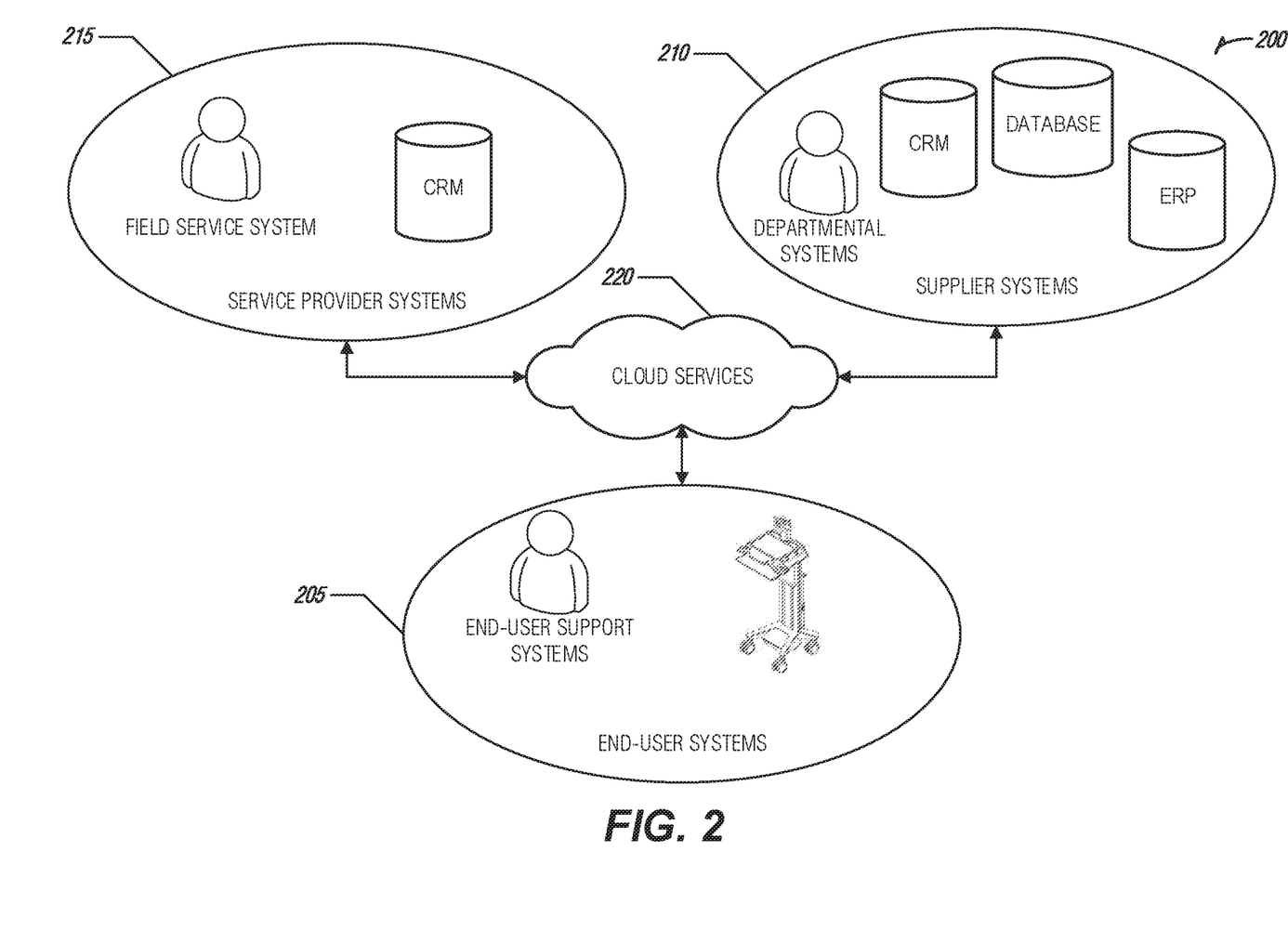
FIG. 2 is a block diagram of data network entities for electronic tel device monitoring, according to an embodiment.

FIG. 2 is a block diagram of data network entities 200 for electronic telemetry-based device monitoring, according to an embodiment. The data network entities 200 may transmit and receive data (e.g., sensor data, instructions, etc.) as described in FIG. 1.

The data network entities 200 may include end-user systems 205, supplier systems 210, service provider systems 215, etc. The end-user systems may include a variety of systems including electronic devices (e.g., electronic device 105, etc.), end-user support systems, etc. The supplier systems 210 may include a variety of systems including an enterprise resource planning (ERP) system, databases, a customer relationship management (CRM) system, departmental systems, etc. The end-user systems 205, the supplier systems 210, and the service provider systems 215 may be communicatively coupled via a cloud service platform 220. In an example, the cloud services platform 220 may include a network management server (e.g., network management server 125 as described in FIG. 1, etc.). In another example, the network management server may be a member of the end-user systems 205, the supplier systems 210, and/or the service provider systems 215.

The electronic devices may transmit (e.g., via wireless network, wired network, cellular network, etc.) a set of sensor data to the cloud service platform 220. The set of sensor data may describe operational status of one or more components of the electronic device. The set of sensor data may be evaluated to determine if the one or more components is operating outside of normal operating conditions or has an operational status that indicates remediation (e.g., component replacement, parameter adjustment, etc) may be necessary. Based on the evaluation, instructions may be transmitted to one or more systems of the end-user systems 205, the supplier systems 210, and the service provider systems 215. The instructions may, individually or in combination, be designed to mitigate any anomalies in the operational status of the one or more components. In an example, the instructions may cause records of the operational status to be created in one or more systems of the end-user systems 205, the supplier systems 210, and the service provider systems 215. These records may be accessed in the future in troubleshooting an issue with the one or more components, future research and development of the one or more components, operational trend analysis of the one or more components, etc, FIG. 3 is a block diagram of an example of a sensor network 300 for electronic telemetry-based device monitoring, according to an embodiment. The sensor network 300 may provide features as described in FIGS. 1 and 2.

The sensor network 300 may include a sensor controller 305. The sensor controller 305 may include a variety of component including a processor 310 (e.g., element 502 as described in FIG. 5, etc.), memory 315 (e.g., elements 504, 506 as described in FIG. 5, etc.), storage 320 (e.g., element 516 as described in FIG. 5, etc.), an onboard sensor 325 (e.g., embedded physical sensor, embedded logical sensor, etc.), and an input/output controller 330 (e.g., elements 512, 528 as described in FIG. 5, etc.).

The sensor network 300 may include a sensor array that may include the onboard sensor 325, a first sensor 335, a second sensor 340, and additional n sensors 345. The sensors may be communicatively coupled (e.g., via wired network, wireless network, shared bus, cellular network, short-wave radio, etc.) to the sensor controller 305 via, the input/output controller.

The memory 315 may include instructions for causing the processor 310 to collect sensor data (e.g., sensor readings, etc.) from the sensors of the sensor array and may store the sensor data in storage 320. The network transceiver 350 may transmit the sensor data to a cloud service platform via the network 355. The network transceiver 350 may communicate with the network 355 via wired network, wireless network, cellular network, short-wave radio, etc. In an example, the network transceiver 350 may use NWT and a publish-subscribe model to reduce network utilization and power consumption.

The network transceiver 350 may receive instructions from the cloud service platform which may be placed in the storage 320 and memory 315. When executed, the instructions may cause the processor 310 to perform operations to adjust (e.g., via the input/output controller 330, etc.) an operating parameter of an electronic device that includes the sensor controller 305. For example, ambient light sensor data may be transmitted to the cloud service platform and instructions may be received the adjust a lighting device of the electronic device upon receipt of a signal from an external device. For example, a signal may be received from a smart lighting switch in a hospital room and upon receipt of a signal indicating the ambient lighting of the hospital room has been lowered, instructions to lower or turn off a floor lighting component of the electronic device may be triggered. In another example, the instructions may include a lighting schedule and power to the lighting component may be adjusted based on the lighting schedule.

Figure 4:
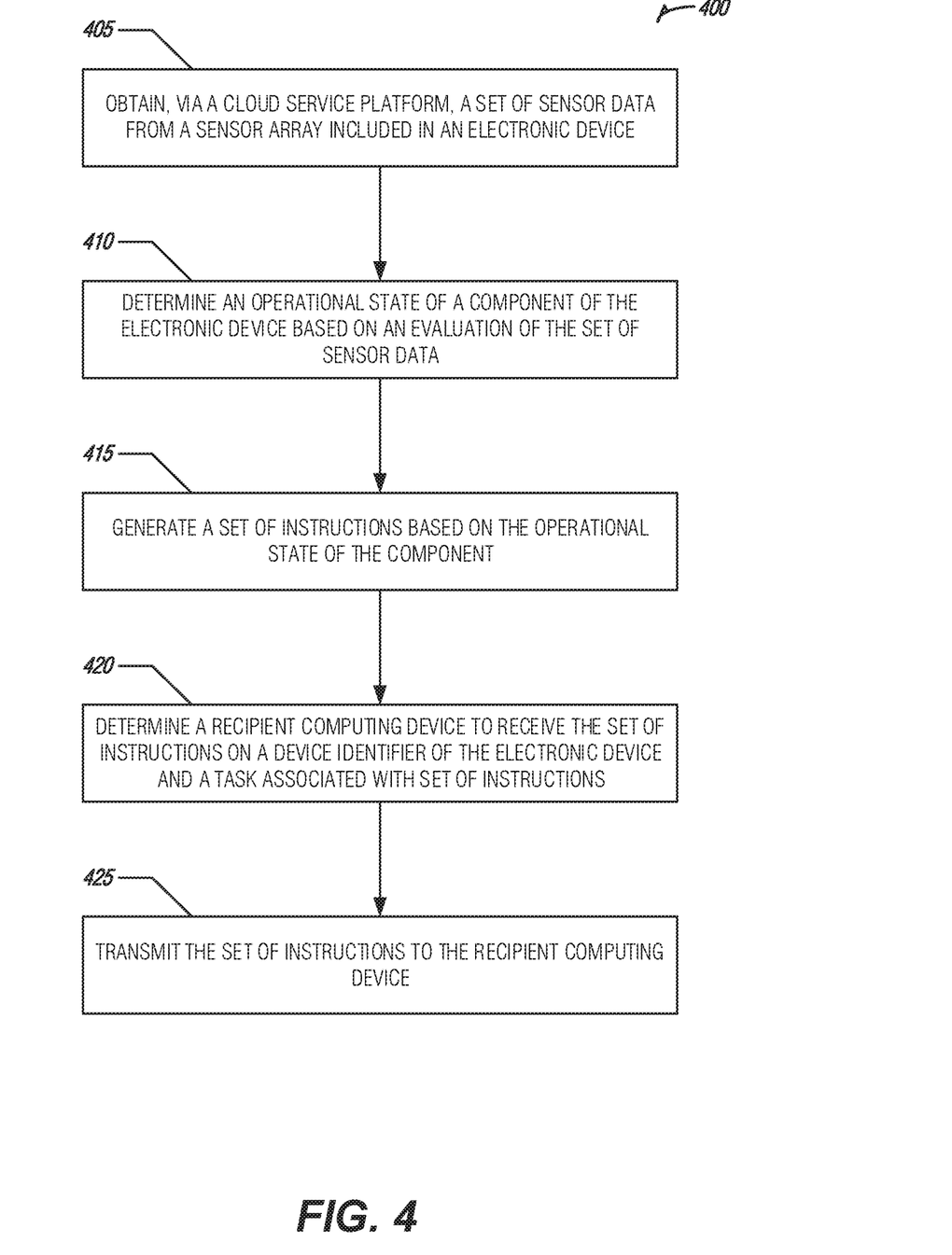
FIG. 4 illustrates an example of a method for electronic telemetry-based device monitoring, according to an embodiment.

FIG. 4 illustrates an example of a method 400 for electronic telemetry-based device monitoring, according to an embodiment. The method 400 may provide features as described in FIGS. 1-3.

A set of sensor data may be obtained (e.g., by the input/output controller 135 as described in FIG. 1, etc.) via a cloud service platform from a sensor array included in an electronic device (e.g., at operation 405). In an example, the sensor array may include at least one sensor selected from a group comprising: a power state sensor, a voltage sensor, an electrical current sensor, a battery temperature sensor, an ambient temperature sensor, a battery capacity sensor, and a battery cycle sensor. In an example, the electronic device may be located in a medical treatment facility.

An operational state of a component of the electronic device may be determined (e.g., by the operational state detector 140 as described in FIG. 1, etc.) based on an evaluation (e.g., by the comparator 145 as described in FIG. 1, etc.) of the set of sensor data (e.g., at operation 410). In an example, the sensor array may include a cycle sensor for the component and the evaluation of the set of sensor data to determine the operational state of the component may include a comparison of a number of cycles of the component observed by the cycle sensor to a cycle threshold for the component. Upon a determination that the number of cycles is at least equal to the cycle threshold, the operational state of the component may be determined to be end-of-life.

In an example, a future failure of the component may be predicted based on the evaluation of the set of sensor data and the evaluation may include a comparison of the set of sensor data to a predictive failure model for the component. The set of instructions may include instructions for mitigation of the future failure.

A set of instructions may be generated (e.g., by the instructions set generator 150 as described in FIG. 1, etc.) based on the operational state of the component (e.g., at operation 415).

A recipient computing device may be determined (e.g., by the data communication router 155, etc.) to receive the set of instructions based on a device identifier of the electronic device and a task associated with set of instructions (e.g., at operation 420). In an example, the recipient device may be a portable device associated with the device identifier and the set of instructions may include instructions that cause the portable device to display operational data for the electronic device that includes the operational state of the component. In another example, the recipient device may be a computing device associated with an owner of the electronic device based on the device identifier and the set of instructions may include instructions that cause the computing device associated with the owner to store operational data for the electronic device that include the operational state of the component, in yet another example, the recipient device may be a customer relationship management computing device and the set of instructions may include instructions that cause the customer relationship management computing device to store operational data for the electronic device that includes the operational state of the component in a record associated with an owner of the electronic device based on the device identifier.

The set of instructions may be transmitted (e.g., by the input/output controller 135 as described in FIG. 1, etc.) to the recipient computing device (e.g., at operation 425). In an example, the set of instructions may include instructions to transmit an electronic order for a replacement component to a supplier of the component and the recipient computing device may be an order processing computing system of the supplier. In another example, the set of instructions may include instructions to transmit an electronic service workorder to a service provider of the electronic device based on the device identifier of the electronic device and the recipient computing device may be a workorder processing system of the service provider.

In an example, a set of fulfillment instructions and a set of record creation instructions may be generated based on the operational state of the component. An owner of the electronic device may be determined based on a device identifier of the electronic device, One or more fulfillment recipient computing devices to receive the set of instructions may be determined based on the device identifier and a task associated with set of instructions. At least a subset of the set of fulfillment instructions may be transmitted to the one or more fulfillment recipient computing devices and the set of record creation instructions may be transmitted to an owner support computing device of the owner and a customer relationship management computing device of a supplier of the electronic device.

In an example, a set of sensor data may be collected from a sensor array. The set of sensor data may describe the operating state of a component of a mobile electronic cart apparatus. The set of sensor data may be transmitted via a transceiver to a cloud service platform. A set of instructions may be received via the transceiver based on an evaluation of the set of sensor data and an operating parameter of the component may be adjusted using the set of instructions. In an example, the set of instructions may include an instruction to adjust the operating parameter of the component based on a signal from a device external to the mobile electronic cart apparatus. In an example, the sensor array may include an ambient light sensor and the set of instructions may include an instruction to adjust a power level applied to a lighting component of the mobile electronic cart apparatus based on receipt of the signal from the device external to the mobile cart apparatus.

Figure 5:
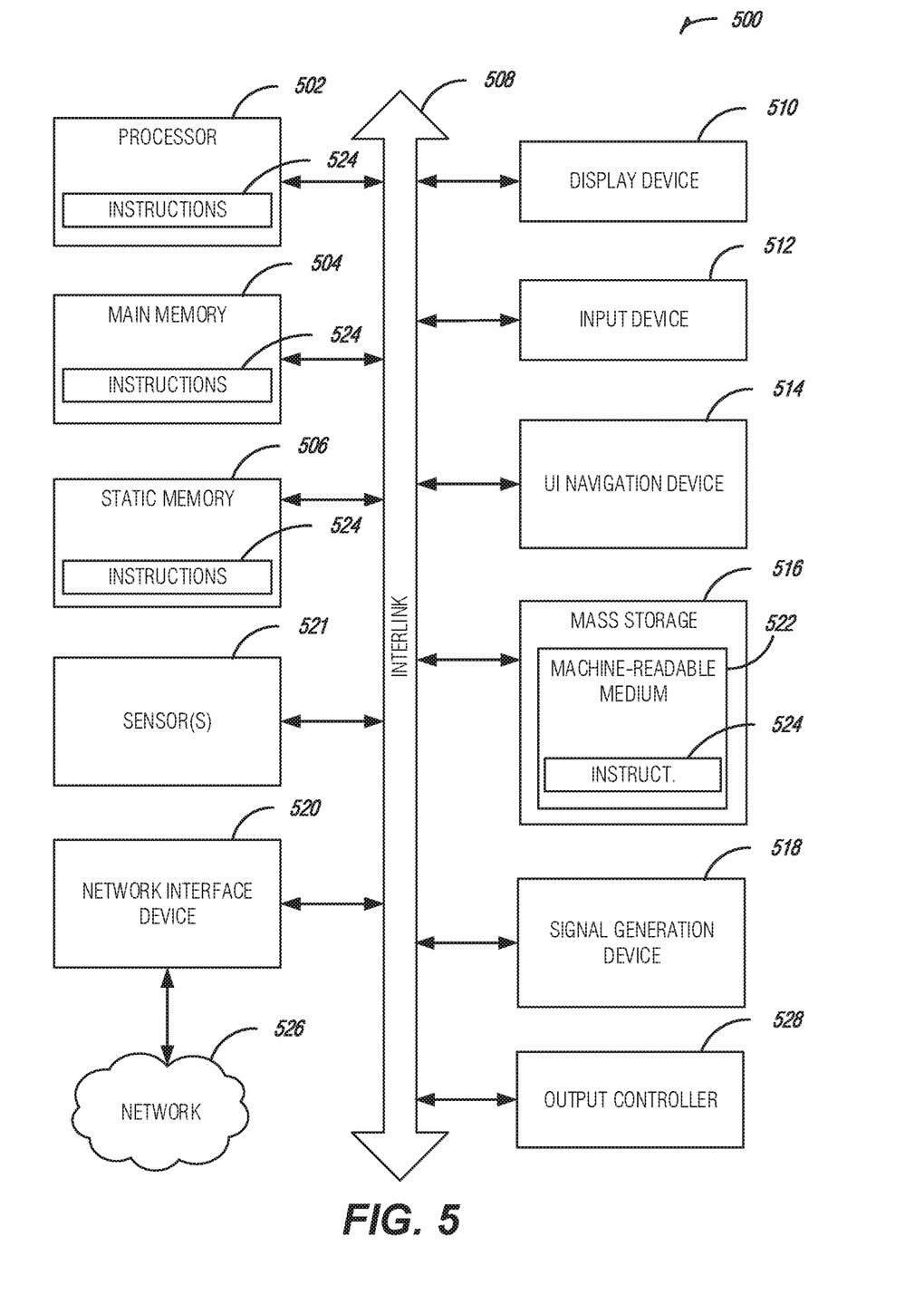
FIG. 5 is a block diagram illustrating an example of a machine upon which one or more embodiments may be implemented.

FIG. 5 illustrates a block diagram of an example machine 500 upon which any one or more of the techniques (e.g., methodologies) discussed herein may perform. In alternative embodiments, the machine 500 may operate as a standalone device or may be connected (e.g., networked) to other machines. In a networked deployment, the machine 500 may operate in the capacity of a server machine, a client machine, or both in server-client network environments. In an example, the machine 500 may act as a peer machine in peer-to-peer (P2P) (or other distributed) network environment. The machine 500 may be a personal computer (PC), a tablet PC, a set-top box (SIB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 500 may include a hardware processor 502 (e.g., a central processing unit (CPU), a graphics processing unit (GPU), a hardware processor core, or any combination thereof), a main memory 504 and a static memory 506, some or all of which may communicate with each other via an interlink (e.g., bus) 508. The machine 500 may further include a display unit 510, an alphanumeric input device 512 (e.g., a keyboard), and a user interface (UI) navigation device 514 (e.g., a mouse). In an example, the display unit 510, input device 512 and UI navigation device 514 may be a touch screen display. The machine 500 may additionally include a storage device (e.g., drive unit) 516, a signal generation device 518 (e.g., a speaker), a network interface device 520, and one or more sensors 521, such as a global positioning system (GPS) sensor, compass, accelerometer, or other sensors. The machine 500 may include an output controller 528, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 516 may include a machine readable medium 522 on which is stored one or more sets of data structures or instructions 524 (e.g., software) embodying or utilized by any one or more of the techniques or functions described herein. The instructions 524 may also reside, completely or at least partially, within the main memory 504, within static memory 506, or within the hardware processor 502 during execution thereof by the machine 500. In an example, one or any combination of the hardware processor 502, the main memory 504, the static memory 506, or the storage device 516 may constitute machine readable media.

While the machine readable medium 522 is illustrated as a single medium, the term "machine readable medium" may include a single medium or multiple media (e.g., a centralized or distributed database, and/or associated caches and servers) configured to store the one or more instructions 524.

The term "machine readable medium" may include any medium that is capable of storing, encoding, or carrying instructions for execution by the machine 500 and that cause the machine 500 to perform any one or more of the techniques of the present disclosure, or that is capable of storing, encoding or carrying data structures used by or associated with such instructions. Non-limiting machine readable medium examples may include solid-state memories, and optical and magnetic media. In an example, machine readable media may exclude transitory propagating signals (e.g., non-transitory machine-readable media). Specific examples of non-transitory machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 524 may further be transmitted or received over a communications network 526 using a transmission medium via the network interface device 520 utilizing any one of a number of transfer protocols (e.g., frame relay, internee protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as IEEE 802.16 family of standards known as WiMax®), IEEE 80115.4 family of standards, peer-to-peer (P2P) networks, 3rd Generation Partnership Project (3GPP) standards for 4G and 5G wireless communication including: 3GPP Long-Term evolution (LTE) family of standards, 3GPP LTE Advanced family of standards, 3GPP LTE Advanced Pro family of standards, 3GPP New Radio (NR) family of standards, among others. In an example, the network interface device 520 may include one or more physical jacks (e.g., Ethernet, coaxial, or phone jacks) or one or more antennas to connect to the communications network 526. In an example, the network interface device 520 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 500, and includes digital or analog communications signals or other intangible medium to facilitate communication of such software.

Additional Notes & Examples

Example 1 is a method for monitoring an electronic device including a sensor array installed in a location, the method comprising: obtaining, via a cloud service platform, a set of sensor data from the sensor array included in the electronic device; determining an operational state of a component of the electronic device based on an evaluation of the set of sensor data; generating a set of instructions based on the operational state of the component; determining a recipient computing device to receive the set of instructions based on a device identifier of the electronic device and a task associated with set of instructions; and transmitting the set of instructions to the recipient computing device.

In Example 2, the subject matter of Example 1 includes, wherein the set of instructions includes instructions to transmit an electronic order for a replacement component to a supplier of the component, and wherein the recipient computing device is an order processing computing system of the supplier.

In Example 3, the subject matter of Examples 1-2 includes, wherein the set of instructions includes instructions to transmit an electronic service workorder to a service provider of the electronic device based on the device identifier of the electronic device, and wherein the recipient computing device is a workorder processing system of the service provider.

In Example 4, the subject matter of Examples 1-3 includes, wherein the sensor array includes a cycle sensor for the component, and the evaluation of the set of sensor data to determine the operational state of the component further comprises: comparing a number of cycles of the component observed by the cycle sensor to a cycle threshold for the component; and upon determining that the number of cycles is at least equal to the cycle threshold, determining the operational state of the component to be end-of-life.

In Example 5, the subject matter of Examples 1-4 includes, wherein the sensor array includes at least one sensor selected from a group comprising: a power state sensor, a voltage sensor, an electrical current sensor, a battery temperature sensor, an ambient temperature sensor, a battery capacity sensor, and a battery cycle sensor.

In Example 6, the subject matter of Examples 1-5 includes, wherein the recipient device is a portable device associated with the device identifier and the set of instructions includes instructions that cause the portable device to display operational data for the electronic device including the operational state of the component.

In Example 7, the subject matter of Examples 1-6 includes, wherein the recipient device is a computing device associated with an owner of the electronic device based on the device identifier and the set of instructions includes instructions that cause the computing device associated with the owner to store operational data for the electronic device including the operational state of the component.

In Example 8, the subject matter of Examples 1-7 includes, wherein the recipient device is a customer relationship management computing device and the set of instructions includes instructions that cause the customer relationship management computing device to store operational data for the electronic device including the operational state of the component in a record associated with an owner of the electronic device based on the device identifier.

In Example 9, the subject matter of Examples 1-8 includes, predicting a future failure of the component based on the evaluation of the set of sensor data, wherein the evaluation includes comparing the set of sensor data to a predictive failure model for the component, wherein the set of instructions include instructions for mitigating the future failure.

In Example 10, the subject matter of Examples 1-9 includes, wherein the location is a medical treatment facility.

Example 11 is a system for monitoring an electronic device including a sensor array installed in a location, the system comprising: at least one processor; and memory including instructions that, when executed by the at least one processor, cause the at least one processor to perform operations to: obtain, via a cloud service platform, a set of sensor data from the sensor array included in the electronic device; determine an operational state of a component of the electronic device based on an evaluation of the set of sensor data; generate a set of instructions based on the operational state of the component; determine a recipient computing device to receive the set of instructions based on a device identifier of the electronic device and a task associated with set of instructions; and transmit the set of instructions to the recipient computing device.

In Example 12, the subject matter of Example 11 includes, wherein the set of instructions includes instructions to transmit an electronic order for a replacement component to a supplier of the component, and wherein the recipient computing device is an order processing computing device of the supplier.

In Example 13, the subject matter of Examples 11-12 includes, wherein the set of instructions includes instructions to transmit an electronic service workorder to a service provider of the electronic device based on the device identifier of the electronic device, and wherein the recipient computing device is a workorder processing computing device of the service provider.

In Example 14, the subject matter of Examples 11-13 includes, wherein the sensor array includes a cycle sensor for the component, and the instructions to evaluate the set of sensor data to determine the operational state of the component further comprises instructions to: compare a number of cycles of the component observed by the cycle sensor to a cycle threshold for the component; and upon a determination that the number of cycles is at least equal to the cycle threshold, determine the operational state of the component to be end-of-life.

In Example 15, the subject matter of Examples 11-14 includes, wherein the sensor array includes at least one sensor selected from a group comprising: a power state sensor, a voltage sensor, an electrical current sensor, a battery temperature sensor, an ambient temperature sensor, a battery capacity sensor, and a battery cycle sensor.

In Example 16, the subject matter of Examples 11-15 includes, wherein the recipient device is a portable device associated with the device identifier and the set of instructions includes instructions that cause the portable device to display operational data for the electronic device including the operational state of the component.

In Example 17, the subject matter of Examples 11-16 includes, wherein the recipient device is a computing device associated with an owner of the electronic device based on the device identifier and the set of instructions includes instructions that cause the computing device associated with the owner to store operational data for the electronic device including the operational state of the component.

In Example 18, the subject matter of Examples 11-17 includes, wherein the recipient device is a customer relationship management computing device and the set of instructions includes instructions that cause the customer relationship management computing device to store operational data for the electronic device including the operational state of the component in a record associated with an owner of the electronic device based on the device identifier.

In Example 19, the subject matter of Examples 11-18 includes, instructions to predict a future failure of the component based on the evaluation of the set of sensor data, wherein the instructions to evaluate the set of sensor data includes instructions to compare the set of sensor data to a predictive failure model for the component, wherein the set of instructions include instructions to mitigate the future failure.

In Example 20, the subject matter of Examples 11-19 includes, wherein the location is a medical treatment facility.

Example 21 is at least one non-transitory machine-readable storage medium including instructions for monitoring an electronic device including a sensor array installed in a location that, when executed by at least one processor, cause the at least one processor to perform operations to: obtain, via a cloud service platform, a set of sensor data from the sensor array included in the electronic device; determine an operational state of a component of the electronic device based on an evaluation of the set of sensor data; generate a set of instructions based on the operational state of the component; determine a recipient computing device to receive the set of instructions based on a device identifier of the electronic device and a task associated with set of instructions; and transmit the set of instructions to the recipient computing device.

In Example 22, the subject matter of Example 21 includes, wherein the set of instructions includes instructions to transmit an electronic order for a replacement component to a supplier of the component, and wherein the recipient computing device is an order processing computing device of the supplier.

In Example 23, the subject matter of Examples 21-22 includes, wherein the set of instructions includes instructions to transmit an electronic service workorder to a service provider of the electronic device based on the device identifier of the electronic device, and wherein the recipient computing device is a workorder processing computing device of the service provider.

In Example 24, the subject matter of Examples 21-23 includes, wherein the sensor array includes a cycle sensor for the component, and the instructions to evaluate the set of sensor data to determine the operational state of the component further comprises instructions to: compare a number of cycles of the component observed by the cycle sensor to a cycle threshold for the component; and upon a determination that the number of cycles is at least equal to the cycle threshold, determine the operational state of the component to be end-of-life.

In Example 25, the subject matter of Examples 21-24 includes, wherein the sensor array includes at least one sensor selected from a group comprising: a power state sensor, a voltage sensor, an electrical current sensor, a battery temperature sensor, an ambient temperature sensor, a battery capacity sensor, and a battery cycle sensor.

In Example 26, the subject matter of Examples 21-25 includes, wherein the recipient device is a portable device associated with the device identifier and the set of instructions includes instructions that cause the portable device to display operational data for the electronic device including the operational state of the component.

In Example 27, the subject matter of Examples 21-26 includes. Wherein the recipient device is a computing device associated with an owner of the electronic device based on the device identifier and the set of instructions includes instructions that cause the computing device associated with the owner to store operational data for the electronic device including the operational state of the component.

In Example 28, the subject matter of Examples 21-27 includes, wherein the recipient device is a customer relationship management computing device and the set of instructions includes instructions that cause the customer relationship management computing device to store operational data for the electronic device including the operational state of the component in a record associated with an owner of the electronic device based on the device identifier.

In Example 29, the subject matter of Examples 21-28 includes, instructions to predict a future failure of the component based on the evaluation of the set of sensor data, wherein the instructions to evaluate the set of sensor data includes instructions to compare the set of sensor data to a predictive failure model for the component, wherein the set of instructions include instructions to mitigate the future failure.

In Example 30, the subject matter of Examples 21-29 includes, wherein the location is a medical treatment facility.

Example 31 is a system for monitoring an electronic device including a sensor array installed in a location, the system comprising: at least one processor; and memory including instructions that, when executed by the at least one processor, cause the at least one processor to perform operations to: obtain, via a cloud service platform, a set of sensor data from the sensor array included in the electronic device; determine an operational state of a component of the electronic device based on an evaluation of the set of sensor data; generate a set of fulfillment instructions and a set of record creation instructions based on the operational state of the component; determine an owner of the electronic device based on a device identifier of the electronic device; determine one or more fulfillment recipient computing devices to receive the set of instructions based on the device identifier and a task associated with set of instructions; and transmit at least a subset of the set of fulfillment instructions to the one or more fulfillment recipient computing devices and transmit the set of record creation instructions to an owner support computing device of the owner and a customer relationship management computing device of a supplier of the electronic device.

Example 32 is at least one non-transitory machine-readable medium including instructions for monitoring an electronic device including a sensor array installed in a location that, when executed by at least one processor, cause the at least one processor to perform operations to: obtain, via a cloud service platform, a set of sensor data from the sensor array included in the electronic device; determine an operational state of a component of the electronic device based on an evaluation of the set of sensor data; generate a set of fulfillment instructions and a set of record creation instructions based on the operational state of the component; determine an owner of the electronic device based on a device identifier of the electronic device; determine one or more fulfillment recipient computing devices to receive the set of instructions based on the device identifier and a task associated with set of instructions; and transmit at least a subset of the set of fulfillment instructions to the one or more fulfillment recipient computing devices and transmit the set of record creation instructions to an owner support computing device of the owner and a customer relationship management computing device of a supplier of the electronic device.

Example 33 is a method for monitoring an electronic device including a sensor array installed in a location, the method comprising: obtaining, via a cloud service platform, a set of sensor data from the sensor array included in the electronic device; determining an operational state of a component of the electronic device based on an evaluation of the set of sensor data; generating a set of fulfillment instructions and a set of record creation instructions based on the operational state of the component; determining an owner of the electronic device based on a device identifier of the electronic device; determining one or more fulfillment recipient computing devices to receive the set of instructions based on the device identifier and a task associated with set of instructions; and transmitting at least a subset of the set of fulfillment instructions to the one or more fulfillment recipient computing devices and transmitting the set of record creation instructions to an owner support computing device of the owner and a customer relationship management computing device of a supplier of the electronic device.

Example 34 is a mobile electronic cart apparatus comprising: a sensor array communicatively coupled to a sensor controller, the sensor controller comprising: at least one processor; a transceiver; and memory including instructions that, when executed by the at least one processor, cause the at least one processor to perform operations to: collect a set of sensor data from the sensor array, the set of sensor data describing the operating state of a component of the mobile electronic cart apparatus; transmit, via the transceiver, the set of sensor data to a cloud service platform; receive, via the transceiver, a set of instructions based on an evaluation of the set of sensor data; and adjust an operating parameter of the component using the set of instructions.

In Example 35, the subject matter of Example 34 includes, wherein the set of instructions includes an instruction to adjust the operating parameter of the component based on a signal from a device external to the mobile electronic cart apparatus.

In Example 36, the subject matter of Example 35 includes, wherein the sensor array includes an ambient light sensor and the set of instructions include an instruction to adjust a power level applied to a lighting component of the mobile electronic cart apparatus based on receipt of the signal from the device external to the mobile cart apparatus.

Example 37 is a method for monitoring a mobile electronic cart apparatus, the method comprising: collecting a set of sensor data from the sensor array, the set of sensor data describing the operating state of a component of the mobile electronic cart apparatus; transmitting, via a transceiver, the set of sensor data to a cloud service platform; receiving, via the transceiver, a set of instructions based on an evaluation of the set of sensor data; and adjusting an operating parameter of the component using the set of instructions.

In Example 38, the subject matter of Example 37 includes, wherein the set of instructions includes an instruction to adjust the operating parameter of the component based on a signal from a device external to the mobile electronic cart apparatus.

In Example 39, the subject matter of Example 38 includes, wherein the sensor array includes an ambient light sensor and the set of instructions include an instruction to adjust a power level applied to a lighting component of the mobile electronic cart apparatus based on receipt of the signal from the device external to the mobile cart apparatus.

Example 40 is at least one non-transitory machine-readable storage medium including instructions for monitoring a mobile electronic cart apparatus that, when executed by at least one processor, cause the at least one processor to perform operations to: collect a set of sensor data from the sensor array, the set of sensor data describing the operating state of a component of the mobile electronic cart apparatus; transmit, via a transceiver, the set of sensor data to a cloud service platform; receive, via the transceiver, a set of instructions based on an evaluation of the set of sensor data; and adjust an operating parameter of the component using the set of instructions.

In Example 41, the subject matter of Example 40 includes, wherein the set of instructions includes an instruction to adjust the operating parameter of the component based on a signal from a device external to the mobile electronic cart apparatus.

In Example 42, the subject matter of Example 41 includes, wherein the sensor array includes an ambient light sensor and the set of instructions include an instruction to adjust a power level applied to a lighting component of the mobile electronic cart apparatus based on receipt of the signal from the device external to the mobile cart apparatus.

Example 43 is at least one machine-readable medium including instructions that, when executed by processing circuitry, cause the processing circuitry to perform operations to implement of any of Examples 1-42.

Example 44 is an apparatus comprising means to implement of any of Examples 1-42.

Example 45 is a system to implement of any of Examples 1-42.

Example 46 is a method to implement of any of Examples 1-42.

The above detailed description includes references to the accompanying drawings, which form a part of the detailed description. The drawings show, by way of illustration, specific embodiments that may be practiced. These embodiments are also referred to herein as "examples," Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is to allow the reader to quickly ascertain the nature of the technical disclosure and is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the embodiments should be determined with reference to the appended claims, along with the full scope of equivalents to which such claims are entitled.

What is claimed is:

1. A system for monitoring an electronic device including a sensor array installed in a location, the system comprising:
   at least one processor; and
   memory including instructions that, when executed by the at least one processor, cause the at least one processor to perform operations to:
   obtain, via a cloud service platform, a set of sensor data from the sensor array included in the electronic device, the sensor array including at least a height adjustment cycle sensor, and the set of sensor data including at least a lift mechanism activation metric collected by the height adjustment cycle sensor;
   input the set of sensor data including the lift mechanism activation metric into a predictive model to determine an operational state of a component of the electronic device based on an evaluation of the set of sensor data, wherein the operational state includes an estimated time to failure metric output by the predictive model;
   generate a set of fulfillment instructions and a set of record creation instructions based on the operational state of the component, the set of fulfillment instructions including instructions executable by an enterprise resource planning system to automatically place an order for a replacement hardware component of the electronic device, wherein the replacement hardware component includes a lift mechanism component;
   determine an owner of the electronic device based on a device identifier of the electronic device;
   determine one or more fulfillment recipient computing devices to receive the set of instructions based on the device identifier and a task associated with set of instructions; and
   transmit at least a subset of the set of fulfillment instructions to the one or more fulfillment recipient computing devices and transmit the set of record creation instructions to an owner support computing device of the owner and a customer relationship management computing device of a supplier of the electronic device, wherein transmission of the set of fulfillment instructions to the one or more fulfillment recipient computing devices causes, upon receipt, the one or more fulfillment recipient computing devices to automatically place the order for the replacement hardware component of the electronic device using the set of fulfillment instructions.

2. A system for monitoring an electronic device including a sensor array installed in a location, the system comprising:
at least one processor; and
memory including instructions that, when executed by the at least one processor, cause the at least one processor to perform operations to:
obtain, via a cloud service platform, a set of sensor data from the sensor array included in the electronic device, the sensor array including at least a height adjustment cycle sensor, and the set of sensor data including at least a lift mechanism activation metric collected by the height adjustment cycle sensor;
input the set of sensor data including the lift mechanism activation metric into a predictive model to determine an operational state of a component of the electronic device based on an evaluation of the set of sensor data, wherein the operational state includes an estimated time to failure metric output by the predictive model;
generate a set of instructions based on the operational state of the component, the set of instructions including a the set of fulfillment instructions that include instructions that are executable by an enterprise resource planning system to automatically place an electronic order for a replacement hardware component of the electronic device, wherein the replacement hardware component includes a lift mechanism component;
determine a recipient computing device to receive the set of instructions based on a device identifier of the electronic device and a task associated with set of instructions;
transmit the set of instructions to the recipient computing device; and
transmit the set of fulfillment instructions to one or more fulfillment recipient computing devices, wherein, upon receipt, the one or more fulfillment recipient computing devices automatically place the electronic order for the replacement hardware component of the electronic device using the set of fulfillment instructions.

3. The system of claim 2, wherein the set of fulfillment instructions includes instructions to transmit the electronic order for the replacement hardware component to a supplier of the replacement hardware component.

4. The system of claim 2, wherein the set of instructions includes instructions to transmit an electronic service workorder to a service provider of the electronic device based on the device identifier of the electronic device, and wherein the recipient computing device is a workorder processing computing device of the service provider.

5. The system of claim 2, wherein the sensor array includes a cycle sensor for the component, and the instructions to evaluate the set of sensor data to determine the operational state of the component further comprises instructions to:
compare a number of cycles of the component observed by the cycle sensor to a cycle threshold for the component; and
upon a determination that the number of cycles is at least equal to the cycle threshold, determine the operational state of the component to be end-of-life.

6. The system of claim 2, wherein the sensor array further includes at least one sensor selected from a group comprising: a power state sensor, a voltage sensor, an electrical current sensor, a battery temperature sensor, an ambient temperature sensor, and a battery cycle sensor.

7. The system of claim 2, wherein the recipient device is a portable device associated with the device identifier and the set of instructions includes instructions that cause the portable device to display operational data for the electronic device including the operational state of the component.

8. The system of claim 2, wherein the recipient device is a computing device associated with an owner of the electronic device based on the device identifier and the set of instructions includes instructions that cause the computing device associated with the owner to store operational data for the electronic device including the operational state of the component.

9. The system of claim 2, wherein the recipient device is a customer relationship management computing device and the set of instructions includes instructions that cause the customer relationship management computing device to store operational data for the electronic device including the operational state of the component in a record associated with an owner of the electronic device based on the device identifier.

10. The system of claim 2, further comprising instructions to predict a future failure of the component based on the evaluation of the set of sensor data, wherein the instructions to evaluate the set of sensor data includes instructions to compare the set of sensor data to a predictive failure model for the component, wherein the set of instructions include instructions to mitigate the future failure.

11. The system of claim 2, wherein the location is a medical treatment facility.

12. A method for monitoring an electronic device including a sensor array installed in a location, the method comprising:
obtaining, via a cloud service platform, a set of sensor data from the sensor array included in the electronic device, the sensor array including at least a height adjustment cycle sensor, and the set of sensor data including at least a lift mechanism activation metric collected by the height adjustment cycle sensor;
input the set of sensor data including the lift mechanism activation metric into a predictive model for determining an operational state of a component of the electronic device based on an evaluation of the set of sensor data, wherein the operational state includes an estimated time to failure metric output by the predictive model;
generating a set of instructions based on the operational state of the component, the set of instructions including a set of fulfillment instructions that include instructions that are executable by an enterprise resource planning system to automatically place an electronic order for a replacement hardware component of the electronic device, wherein the replacement hardware component includes a lift mechanism component;
determining a recipient computing device to receive the set of instructions based on a device identifier of the electronic device and a task associated with set of instructions;
transmitting the set of instructions to the recipient computing device; and
transmitting the set of fulfillment instructions to one or more fulfillment recipient computing devices, wherein, upon receipt, the one or more fulfillment recipient computing devices automatically place the electronic order for the replacement hardware component of the electronic device using the set of fulfillment instructions.

13. The method of claim 12, wherein the set of fulfillment instructions includes instructions to transmit the electronic order for the replacement hardware component to a supplier of the replacement hardware component.

14. The method of claim 12, wherein the set of instructions includes instructions to transmit an electronic service workorder to a service provider of the electronic device based on the device identifier of the electronic device, and wherein the recipient computing device is a workorder processing system of the service provider.

15. The method of claim 12, wherein the sensor array includes a cycle sensor for the component, and the evaluation of the set of sensor data to determine the operational state of the component further comprises:
    comparing a number of cycles of the component observed by the cycle sensor to a cycle threshold for the component; and
    upon determining that the number of cycles is at least equal to the cycle threshold, determining the operational state of the component to be end-of-life.

16. The method of claim 12, wherein the sensor array further includes at least one sensor selected from a group comprising: a power state sensor, a voltage sensor, an electrical current sensor, a battery temperature sensor, an ambient temperature sensor, and a battery cycle sensor.

17. The method of claim 12, wherein the recipient device is a portable device associated with the device identifier and the set of instructions includes instructions that cause the portable device to display operational data for the electronic device including the operational state of the component.

18. The method of claim 12, wherein the recipient device is a computing device associated with an owner of the electronic device based on the device identifier and the set of instructions includes instructions that cause the computing device associated with the owner to store operational data for the electronic device including the operational state of the component.

19. The method of claim 12, wherein the recipient device is a customer relationship management computing device and the set of instructions includes instructions that cause the customer relationship management computing device to store operational data for the electronic device including the operational state of the component in a record associated with an owner of the electronic device based on the device identifier.

20. The method of claim 12, further comprising predicting a future failure of the component based on the evaluation of the set of sensor data, wherein the evaluation includes comparing the set of sensor data to a predictive failure model for the component, wherein the set of instructions include instructions for mitigating the future failure.

21. The method of claim 12, wherein the location is a medical treatment facility.

22. A mobile electronic cart apparatus comprising:
    a sensor array communicatively coupled to a sensor controller, the sensor controller comprising:
        at least one processor;
        a transceiver; and
        memory including instructions that, when executed by the at least one processor, cause the at least one processor to perform operations to:
            collect a set of sensor data from the sensor array, the set of sensor data describing an operating state of a component of the mobile electronic cart apparatus, the sensor array including at least a height adjustment cycle sensor, and the set of sensor data including at least a lift mechanism activation metric collected by the height adjustment cycle sensor;
            transmit, via the transceiver, the set of sensor data to a cloud service platform;
            receive, via the transceiver, a set of instructions based on an evaluation of the set of sensor data including the lift mechanism activation metric using a predictive model, wherein the set of instructions is based on an operational state, that includes an estimated time to failure metric output by the predictive model, wherein the set of instructions are received in parallel with transmission, by the cloud service platform, of a set of fulfillment instructions that include instructions executable by an enterprise resource planning system, to automatically place an order for a replacement hardware component of the mobile electronic cart apparatus, wherein the replacement hardware component includes a lift mechanism component, the set of fulfillment instructions causing, upon receipt by one or more fulfillment recipient computing devices, the one or more fulfillment recipient computing devices to automatically place the order for the replacement hardware component of the electronic device using the set of fulfillment instructions; and
            adjust an operating parameter of the component using the set of instructions.

23. The mobile electronic cart apparatus of claim 22, wherein the set of instructions includes an instruction to adjust the operating parameter of the component based on a signal from a device external to the mobile electronic cart apparatus.

24. The mobile electronic cart apparatus of claim 23, wherein the sensor array includes an ambient light sensor and the set of instructions include an instruction to adjust a power level applied to a lighting component of the mobile electronic cart apparatus based on receipt of the signal from the device external to the mobile cart apparatus.

* * * * *